(12) United States Patent
Wang

(10) Patent No.: US 6,569,116 B1
(45) Date of Patent: May 27, 2003

(54) INTRAVENOUS FLOW CONTROLLING DEVICE

(76) Inventor: Hsien Tsung Wang, 6 FL. No. 31-23, Tung Tsun Road, Tai Ping City, Taichung County (TW)

(*) Notice: Subject to any disclaimer, the term of this patent is extended or adjusted under 35 U.S.C. 154(b) by 35 days.

(21) Appl. No.: 09/717,076

(22) Filed: Nov. 22, 2000

(51) Int. Cl.7 .............................. A61M 1/00; F16K 1/00
(52) U.S. Cl. ......................... 604/127; 222/66; 251/334; 604/254
(58) Field of Search ............................ 222/66; 604/127, 604/254; 251/334; 137/399, 192, 533

(56) References Cited

U.S. PATENT DOCUMENTS

| | | | |
|---|---|---|---|
| 3,216,419 A | * 11/1965 | Scislowicz | 137/399 |
| 3,227,173 A | * 1/1966 | Bernstein | 137/192 |
| 5,415,325 A | * 5/1995 | Shu | 137/399 X |
| 6,017,332 A | * 1/2000 | Urrutia | 604/254 |

* cited by examiner

*Primary Examiner*—William Wayner
(74) *Attorney, Agent, or Firm*—Troxell Law Office PLLC

(57) ABSTRACT

An intravenous (IV) flow controlling device comprises a flexible open container having a specific gravity less than one and an outer diameter smaller than that of the drip chamber, the container including a spherical bottom portion thinner than the shell upper portion thereof; a first plastic tube coupled to the bottom of the container being in communication with the exit; a flexible reservoir having one end coupled to the first tube; and a second plastic tube coupled to the other end of the reservoir being in communication therewith. The container is submerged as fluid filled in the drip chamber. Fluid flows through the exit, the first plastic tube, the reservoir, and the second plastic tube to cause the container to fall, thereby stopping fluid exiting when the bottom portion of the container clogs the exit and fluid in the drip chamber is used up. The reservoir is capable of being squeezed to force solution stored in the reservoir to reverse flow through the first tube to disengage the container from the exit. The device functions normally when solution is used up, abnormal solution dropping, drip chamber shaken, or drip chamber slanted.

10 Claims, 14 Drawing Sheets

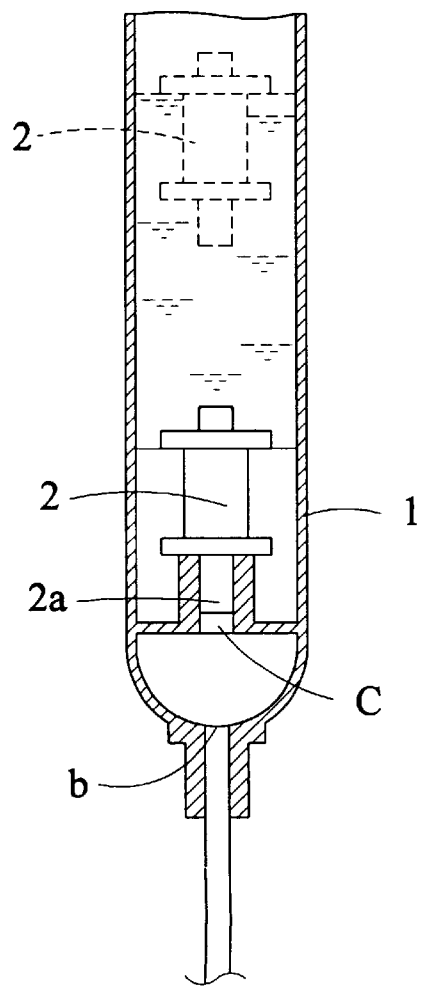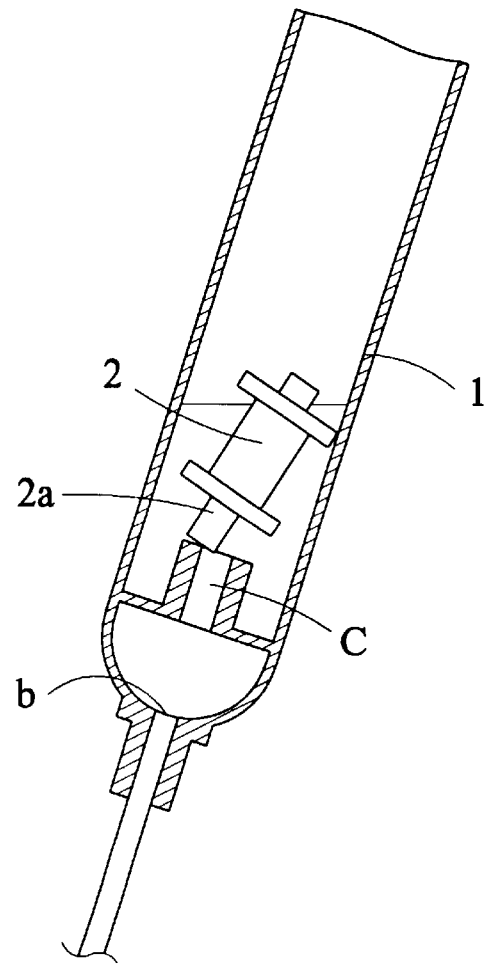
FIG. 11A
PRIOR ART
FIG. 11B
PRIOR ART

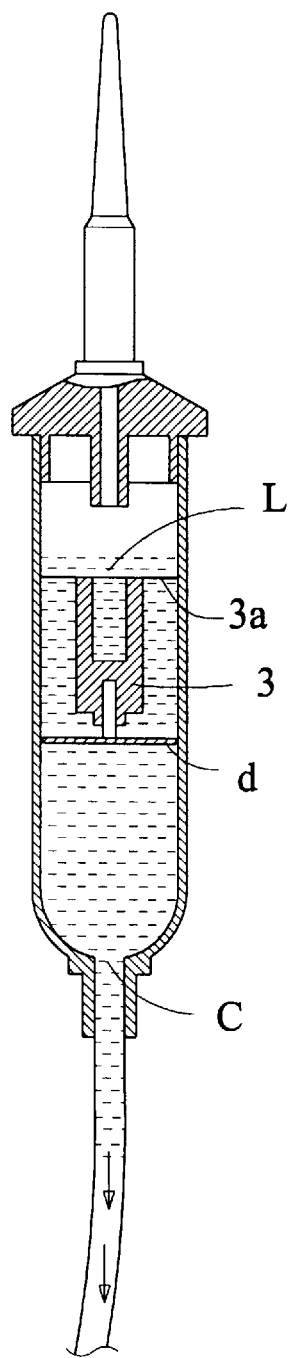
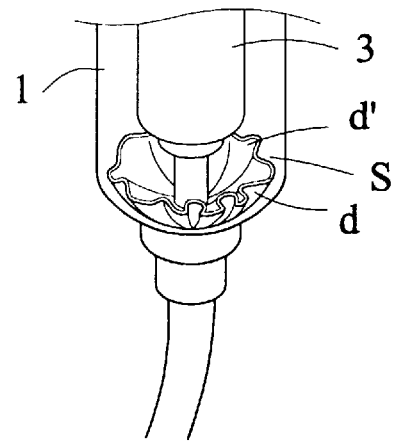
FIG. 12B
PRIOR ART
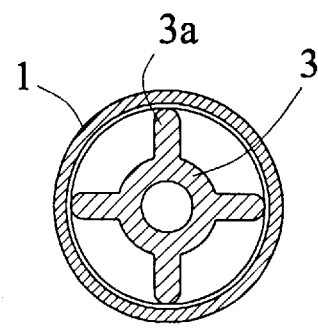
FIG. 12A
PRIOR ART
FIG. 12C
PRIOR ART

INTRAVENOUS FLOW CONTROLLING DEVICE

BACKGROUND OF THE INVENTION

1. Field of the Invention

The present invention relates to an intravenous flow controlling device which functions normally when solution is used up, abnormal solution dropping, drip chamber shaken, or drip chamber slanted.

2. Description of Related Art

Devices for controlling the flow of intravenous (IV) fluids to a patient are known. In general, they are designed to provide a constant fluid flow to patient and an automatic stop is activated once solution is used up for preventing air from injecting into patient. A conventional flow control device is shown in FIGS. 11A and 11B; As shown in FIG. 11A, the device is a float 2 having.a stud 2a underneath. Also, a hole c is provided on a divider for communication between upper and lower portions of drip chamber 1. In operation, float 2 is submerged as solution filled in drip chamber 1. As such, fluid may flow through exit b. The fluid level may drop as fluid exits. Float 2 may fall accordingly due to its weight. Finally, the stud 2a falls into hole c to stop the fluid flow through exit b.

However, the previous design suffered from a disadvantage. In detail, stud 2a may never fall into hole b when drip chamber 1 is shaken by an external force or slanted near the depletion of solution. This immediately causes stud 2a to contact the top of divider (i.e., top periphery of hole c) as shown in FIG. 11B. Now the float 2 is in a dead point. This also compromises the desired auto-stop functionality of the flow control device.

Another conventional flow control device is shown in FIGS. 12A to 12C. The device is a submerged reservoir 3 having a circular plane diaphragm d underneath. In operation, the submerged reservoir 3-is submerged as solution L filled in drip chamber 1. As such, fluid may flow through exit c. The fluid level drops as fluid exits. The submerged reservoir 3 full of solution L may fall accordingly due to its weight. Finally, the circular plane diaphragm d clogs exit c to stop the fluid flow when fluid in the drip chamber 1 is used up.

However, the previous design suffered from a disadvantage. In detail, a number of wrinkles d' may be formed on the periphery of circular plane diaphragm d. As such, many channels s exist for communication with exit c as best illustrated in FIG. 12B. This means that circular plane diaphragm d is not completely adhered to the bottom of drip chamber 1 when solution L in the drip chamber 1 is used up. As such, fluid may pass the exit b through channels s. Further, a plurality of wings 3a (four are shown) are formed on the top periphery of submerged reservoir 3 being in contact with the inner wall of drip chamber 1 for stabilizing the up or down movement of float member 3. However, such design may only functions well when the submerged reservoir 3 has a cylindrical shape or the inner wall of drip chamber 1 is very smooth. Otherwise it may clog on the wall of drip chamber 1, thus compromising the floating functionality of submerged reservoir 3. The case shown in FIGS. 12A to 12C is not desirable since the drip chamber 1 has a concave spherical surface. In view of the above, the desired auto-stop functionality of this flow control device is also compromised.

SUMMARY OF THE INVENTION

It is thus an object of the present invention to provide an intravenous (IV) flow controlling device disposed in a drip chamber having an exit in the bottom. The device comprises a flexible float member having a specific gravity less than one and an outer diameter smaller than that of the drip chamber, the cup member including an upper portion and a spherical bottom portion thinner than the upper portion of the float member member; a first plastic tube coupled to the bottom of the float member being in communication with the exit of the drip chamber; a flexible reservoir having one end coupled to the first tube; and a second plastic tube coupled to the other end of the reservoir being in communication therewith, wherein the float member is submerged as fluid filled in the drip chamber, fluid flows through the exit of the drip chamber, the first plastic tube, the reservoir, and the second plastic tube to cause the float member to fall, thereby stopping fluid exiting when the bottom portion of the float member clogs the exit of the drip chamber and fluid in the drip chamber is used up, and the reservoir is capable of being squeezed to force solution stored in the reservoir to flow through the first tube in reverse direction to disengage the bottom portion of float member from the exit of the drip chamber. Therefore, the IV flow controlling device of the present invention still functions normally when solution is used up, abnormal solution dropping, drip chamber shaken, or drip chamber slanted.

It is another object of the present invention to provide an intravenous (IV) flow controlling device disposed in a drip chamber having an exit in the bottom. The device comprises a flexible float member having a specific gravity less than one and an outer diameter smaller than that of the drip chamber, the float member including an upper portion and a spherical bottom portion thinner than the upper portion of the float member member, wherein the float member is submerged as fluid filled in the drip chamber, fluid flows through the exit of the drip chamber to cause the float member to fall, thereby stopping fluid exiting when the bottom portion of the float member clogs the exit of the drip chamber and fluid in the drip chamber is used up. The IV flow controlling device of the present invention is still functioning normally when solution is used up, abnormal solution dropping, drip chamber shaken, or drip chamber slanted.

In one aspect of the invention, when an abnormal solution dropping such as excessive dripping of solution occurs due to carelessness of operator, the fluid level in the drip chamber is still maintained at a constant. Also, float member immediately falls a distance due to the sensitive design of the invention. Moreover, a strong suction force is formed at exit when float member falls to its lowest position, thereby causing the bottom of float member to clog exit to stop the fluid flow.

The above and other objects, features and advantages of the present invention will become apparent from the following detailed description taken with the accompanying drawings.

BRIEF DESCRIPTION OF THE DRAWINGS

FIG. 11A is a cross-sectional view of a conventional intravenous flow controlling device where the device works normally;

FIG. 11B is similar to FIG. 11A where the functionality of the device of the FIG. 11A compromise due to a shaking or slant;

FIG. 12A is a cross-sectional view of another conventional intravenous flow controlling device;

FIG. 12B is a schematic perspective view showing the functionality of the device of FIG. 12A being compromised due to the wrinkling of the circular plane diaphragm; and FIG. 12C is a cross-sectional view of the reservoir and drip chamber shown in FIG. 12A.

DETAILED DESCRIPTION OF THE PREFERRED EMBODIMENTS

Figure 1A:
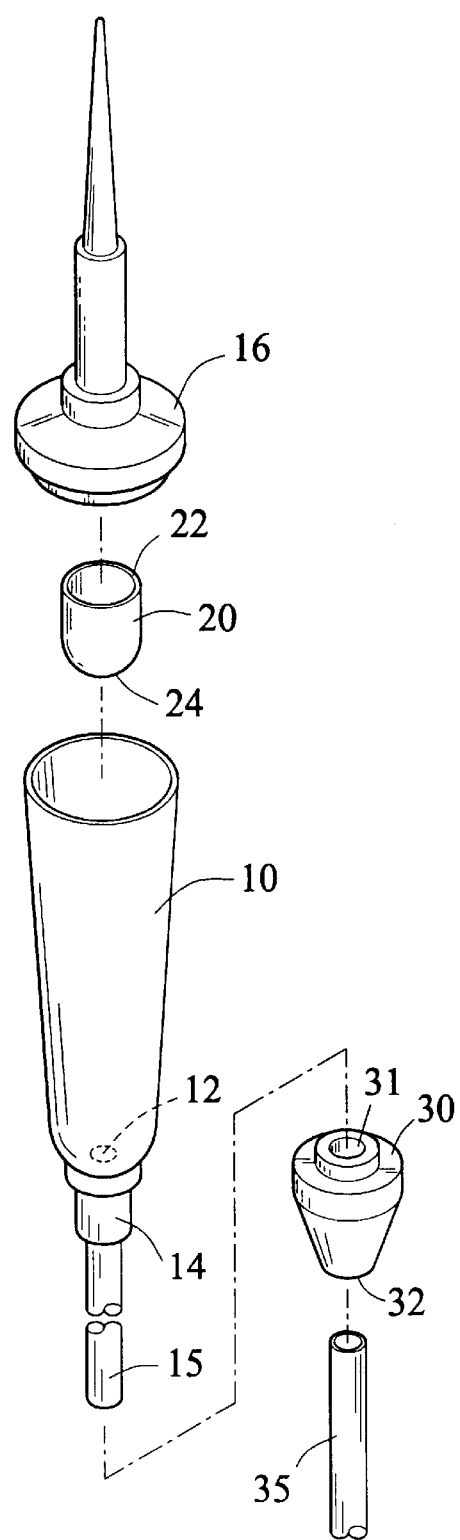
FIG. 1A is a perspective exploded view of a first preferred embodiment of intravenous flow controlling device according to the invention.
Figure 1B:
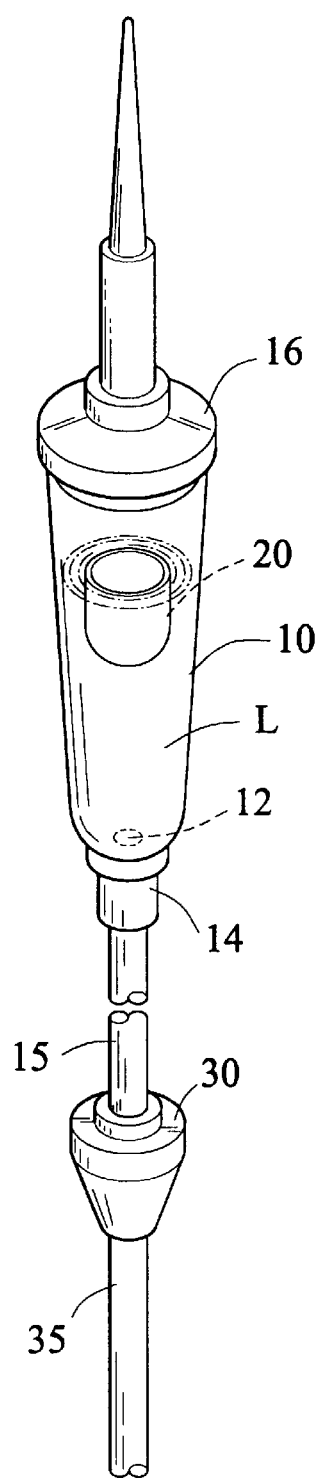
FIG. 1B is a perspective view of the device of FIG. 1A.
Figure 1C:
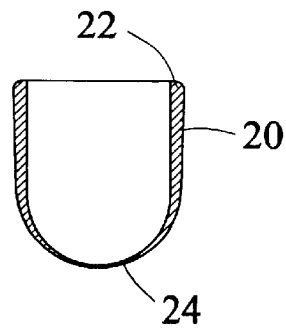
FIG. 1C is a cross-sectional view of float member shown in FIG. 1A.
Figure 1D:
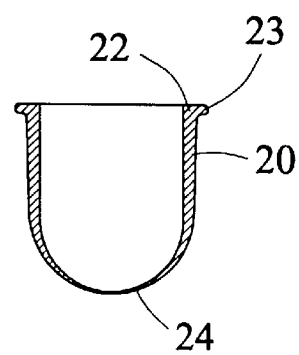
FIG. 1D is a cross-sectional view of another configuration of float member where float member has an annular flange formed on the top periphery thereof.

Referring to FIGS. 1A to 1D, there is shown a first preferred embodiment of intravenous (IV) flow controlling device constructed in accordance with the invention. The device is a float member 20 disposed inside a drip chamber 10. Float member 20 is a flexible and thin member (e.g., made of rubber or plastic) having a thicker upper portion 22 and a thinner spherical bottom portion 24. The specific gravity of float member 20 is slightly smaller than one (1).

Preferably, an annular flange 23 is provided on the top periphery of float member 20 increasing the stability when float member 20 is submerged in the solution. The outer diameter of float member 20 is slightly smaller than that of the drip chamber 10. Drip chamber 10 has an exit 12 in the bottom. A joint 14 is on the underside of drip chamber 10 for coupling to a first plastic tube 15, which is in communication with the solution of drip chamber 10 through exit 12. A cap 16 having a sharp top end is fitted onto the top of cup 10. A reservoir 30 made of flexible material is coupled between first tube 15 on the top and a second plastic tube 35 on the bottom. Reservoir 30 has a top opening 31 and a bottom exit 32.

Figure 2A:
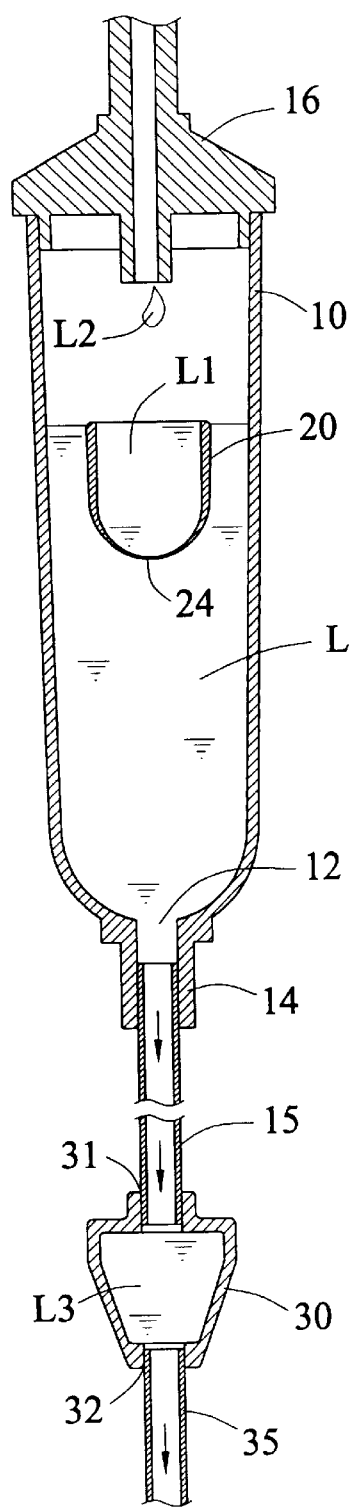
FIG. 2A is a cross-sectional view depicting the operation of the intravenous flow controlling device of FIG. 1A where the device works normally.
Figure 2B:
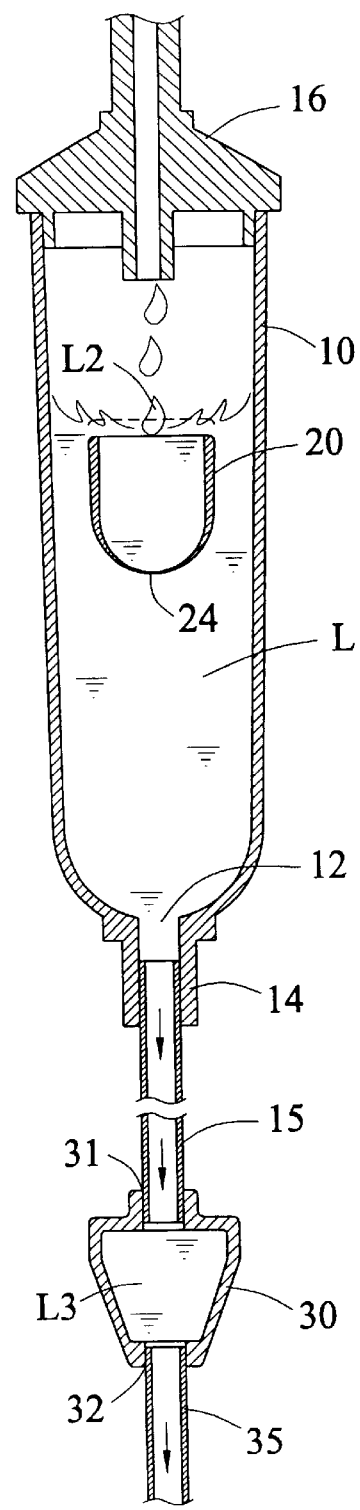
FIG. 2B is similar to FIG. 2A where an abnormal solution dropping occurs.
Figure 2C:
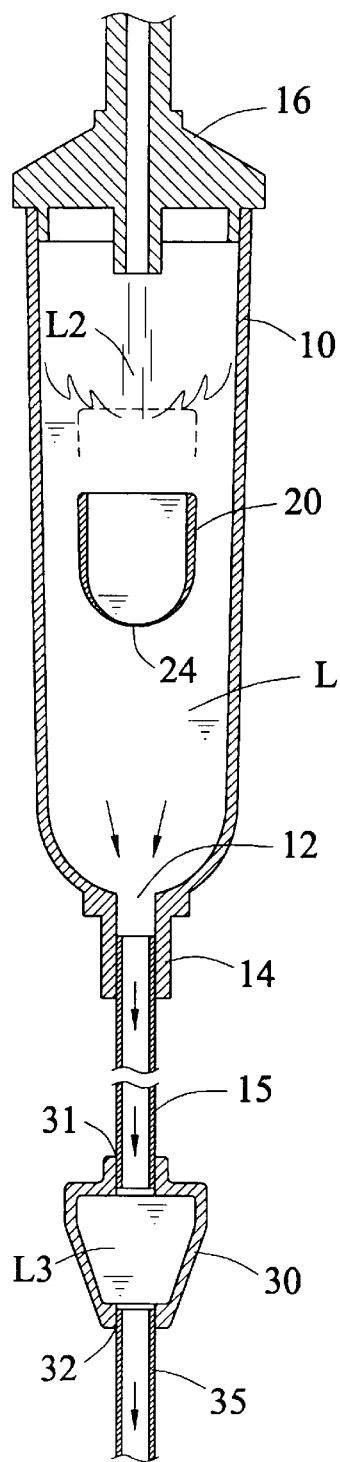
FIG. 2C is similar to FIG. 2A where the float member is going to fall.
Figure 2D:
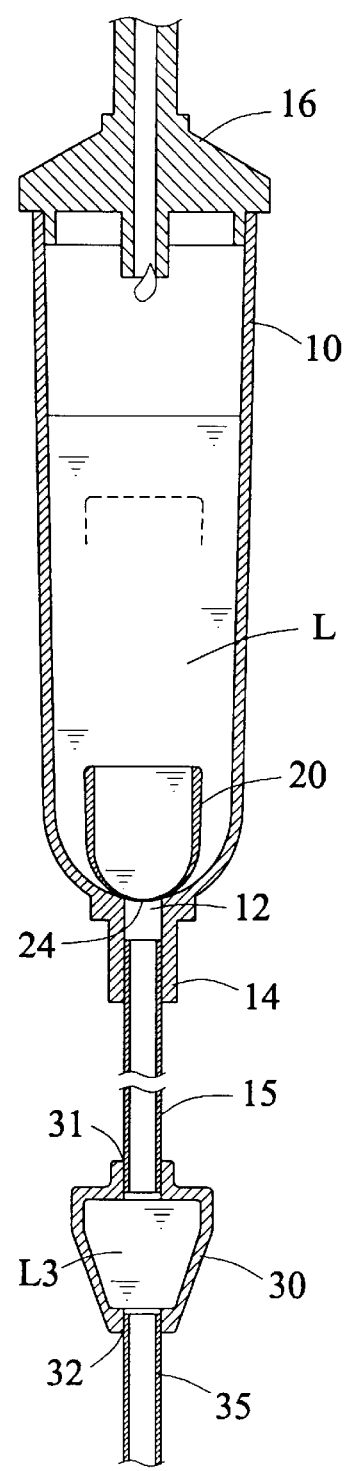
FIG. 2D is similar to FIG. 2A where float member clogs the exit of drip chamber.

Referring to FIGS. 2A to 2D, the operation of the FIG. 1 device will now be described. Float member 20 is submerged as solution filled in drip chamber 10. In this state, the total weight G (i.e., the weight of solution plus the weight of float member 20) is slightly smaller than the buoyancy of solution F. That is, G<F. As such, fluid may flow through exit 12 in a normal dripping of solution. Note that the gravitation of drop is g1. The fluid level may drop as fluid exits. Float member 20 full of solution may fall accordingly due to its weight because G+g1=F (see FIGS. 2A and 2B). As shown in FIGS. 2C and 2D, an abnormal solution dropping (i.e., excessive dripping of solution) occurs due to the carelessness of operator. Note that the gravitation of the abnormal drop is g2. At this time, the fluid level is still maintained at a constant. However, float member 20 will immediately fall a distance due to the sensitive design of the invention. A strong suction force fv is formed at exit 12 when float member 20 falls to its lowest position, thereby causing the bottom 24 of float member 20 to clog exit 12 to stop the fluid flow. This may be best represented by equations below G+g2>F and G+g2+fv>>F.

Figure 3A:
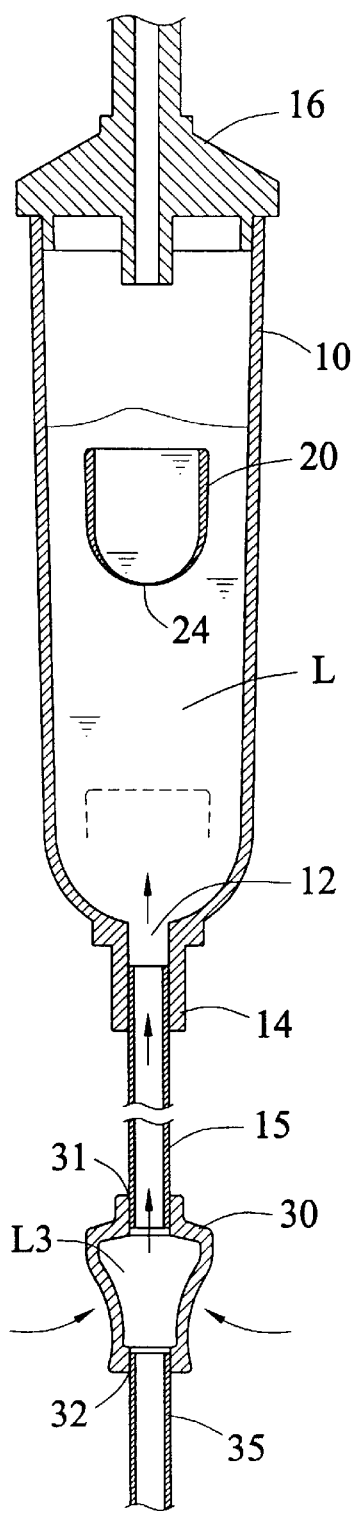
FIG. 3A is a cross-sectional view depicting that the float member is forced to move up by.squeezing a reservoir shown in FIG. 2A.

Referring to FIG. 3A, the process of forcing float member 20 adhered to the exit 12 back to its normal position will now be described. In operation, operator may squeeze reservoir 30 by hand or fingers so as to force solution stored in reservoir 30 to reversely flow upward through first tube 15 to disengage float member 20 from exit 12.

Figure 3B:
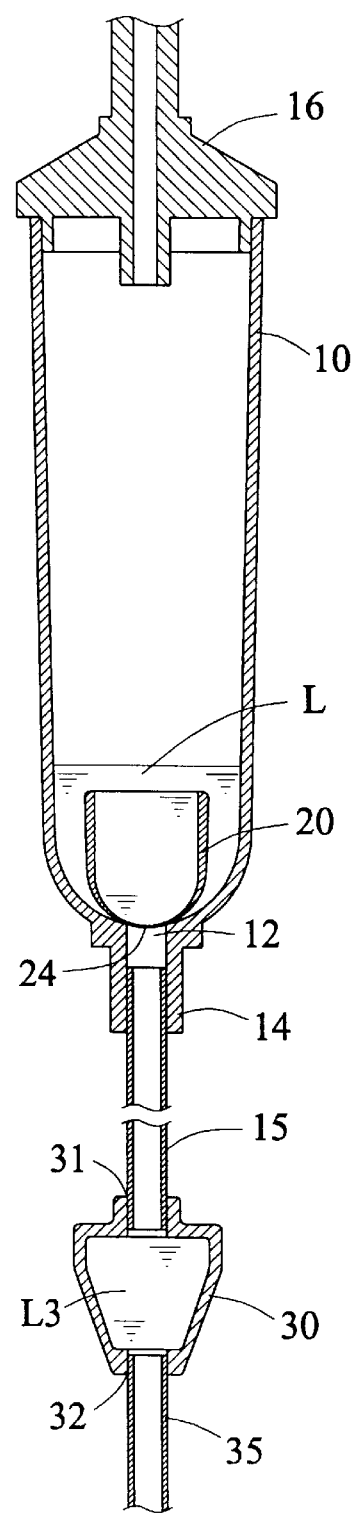
FIG. 3B is similar to FIG. 2A where solution in the drip chamber is nearly used up.

Referring to FIG. 3B, the bottom 24 of float member 20 is adhered to exit 12 by the suction of solution when solution in the drip chamber 10 is nearly used up. This stops the flow of solution.

Figure 4:
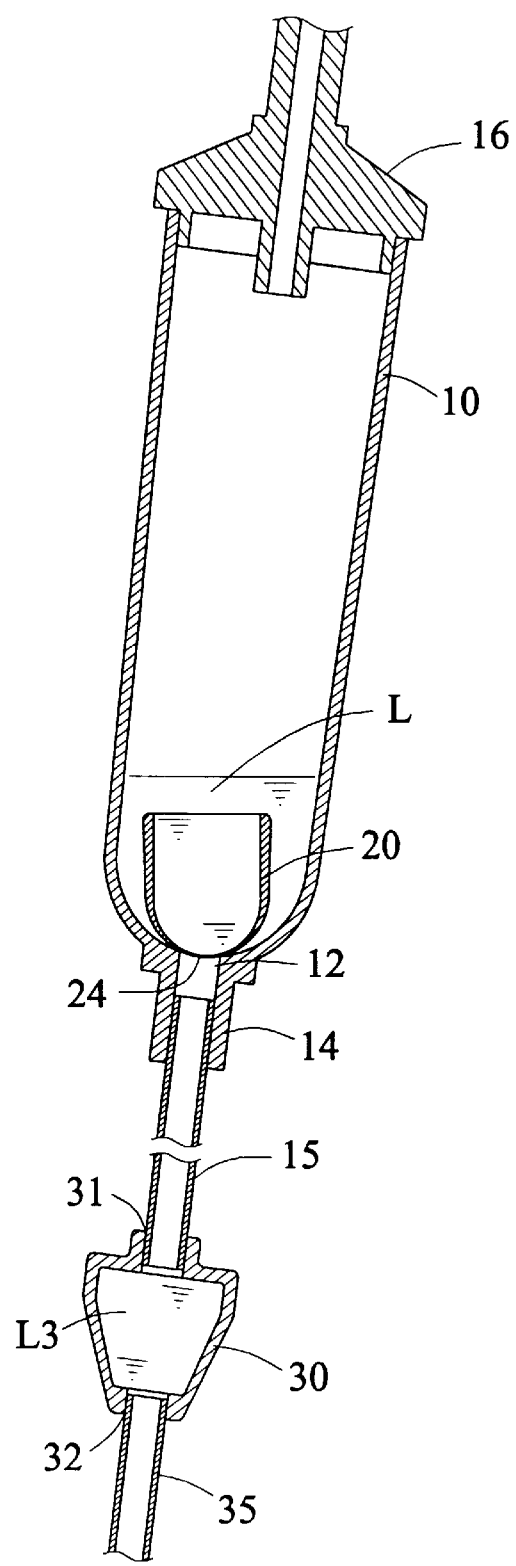
FIG. 4 is similar to FIG. 2A where the bottom of float member still adheres to fluid exit even when float member is slanted.

Referring to FIG. 4, it is seen that the bottom 24 of float member 20 is still adhered to fluid exit 12 even when float member 20 is slanted due to shaking. The functionality of float member 20 is still well maintained. This is the advantage of the invention.

Figure 5A:
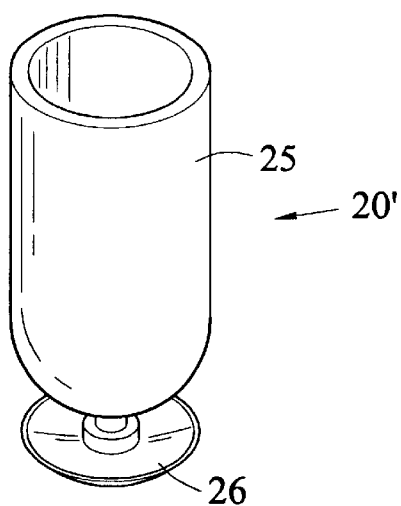
FIG. 5A is a perspective view of a second embodiment of float member.
Figure 5B:
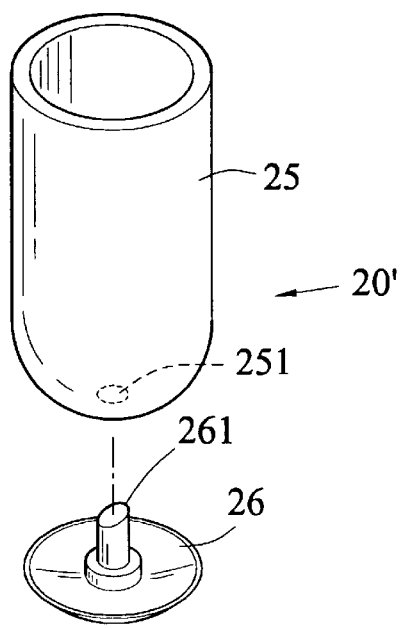
FIG. 5B is a perspective exploded view of FIG. 5A.

FIGS. 5A and 5B illustrates a second embodiment of float member 20' of the invention. Float member 20' comprises a thin shell 25 having a bottom hole 251 and a downwards extending convex diaphragm 26 having an upper stud 261 inserted into the hole 251 for securing to the shell 25. The specific gravity of float member 20' is slightly smaller than one (1). The diameter of shell 25 is slightly smaller than that of the narrower lower portion of drip chamber 10. This has an even better fluid stopping functionality than the float member 20 of the first embodiment.

Figure 6:
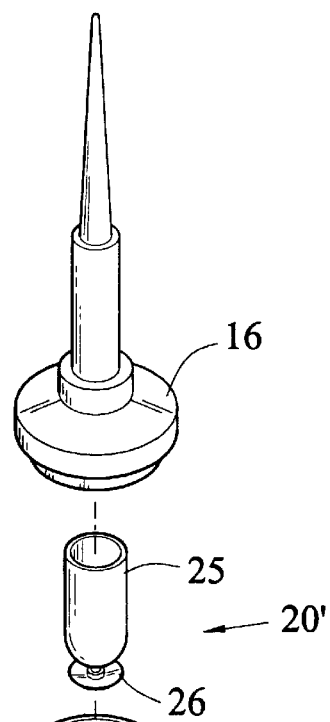
FIG. 6 is a perspective exploded view of a second preferred embodiment of intravenous flow controlling device according to the invention.
Figure 6:
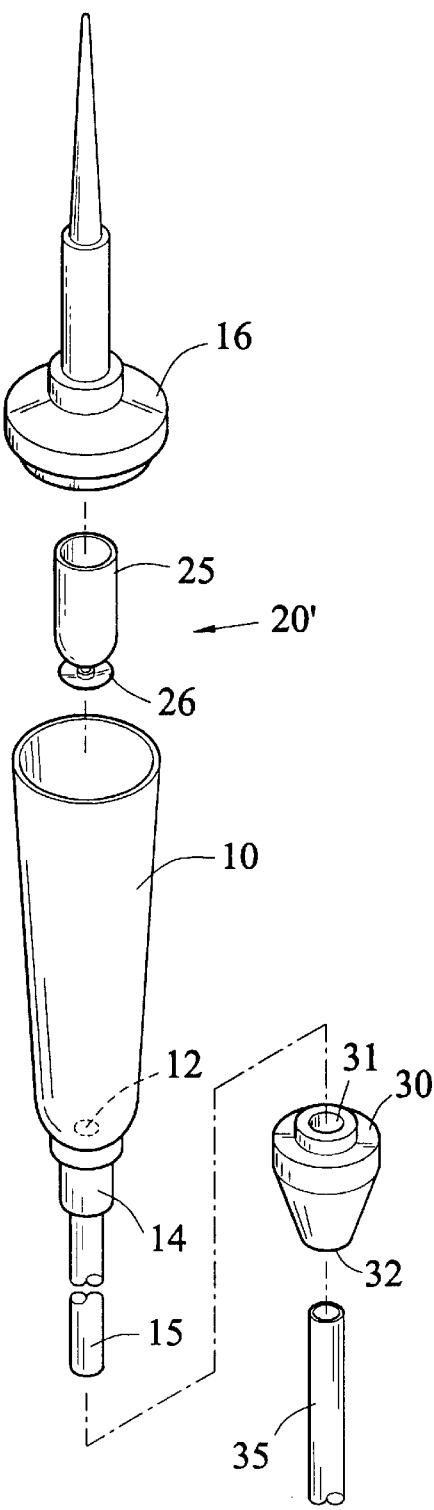

The components shown in FIG. 6 are the same as that shown in FIG. 1A except float member 20 of the first embodiment is replaced by float member 20' of the second embodiment. Thus its detail description is omitted herein for the sake of brevity.

Figure 7:
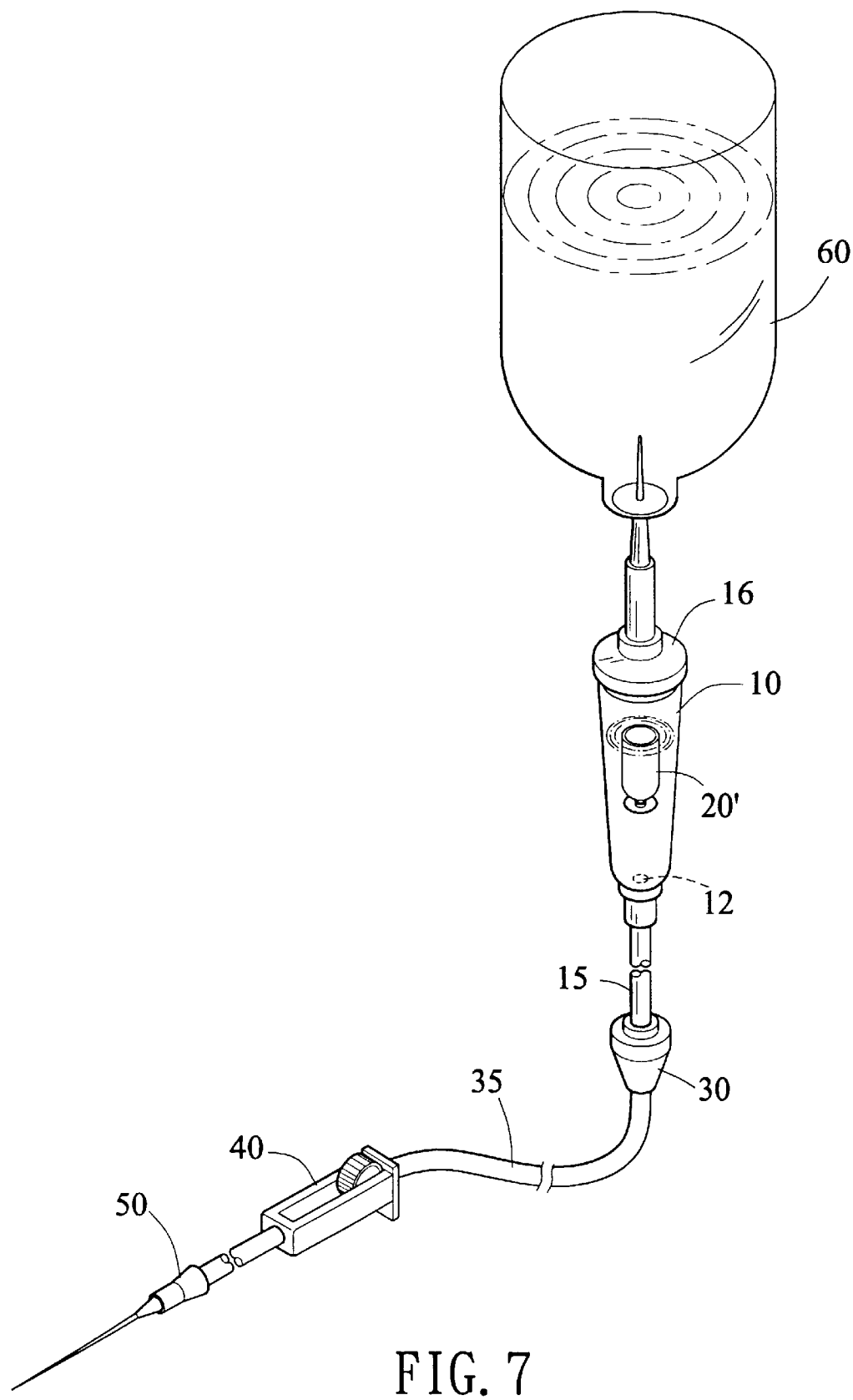
FIG. 7 is a perspective view for schematically depicting the in-use operation of the whole set device of FIG. 6.
Figure 8A:
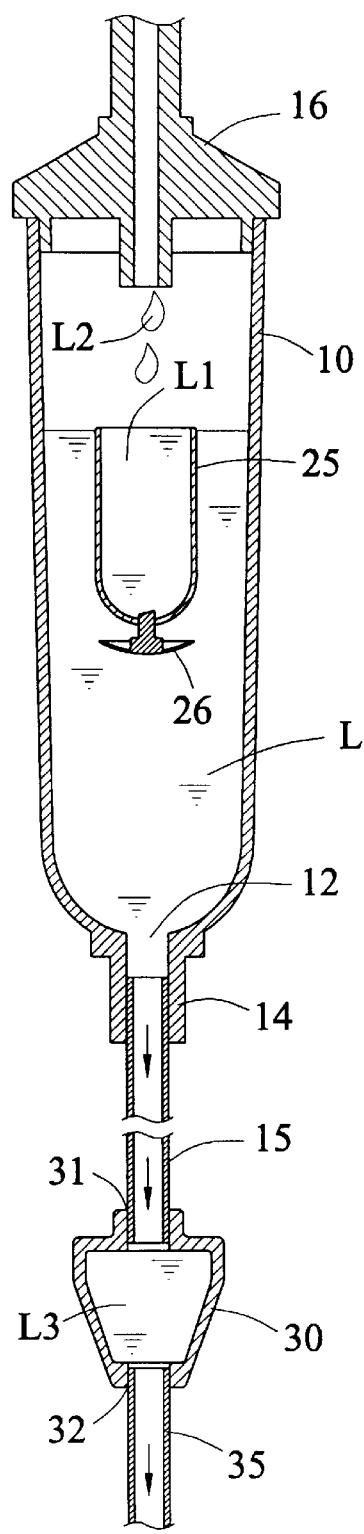
FIG. 8A is a cross-sectional view depicting the operation of the intravenous flow controlling device of FIG. 6 where the device works normally.
Figure 8B:
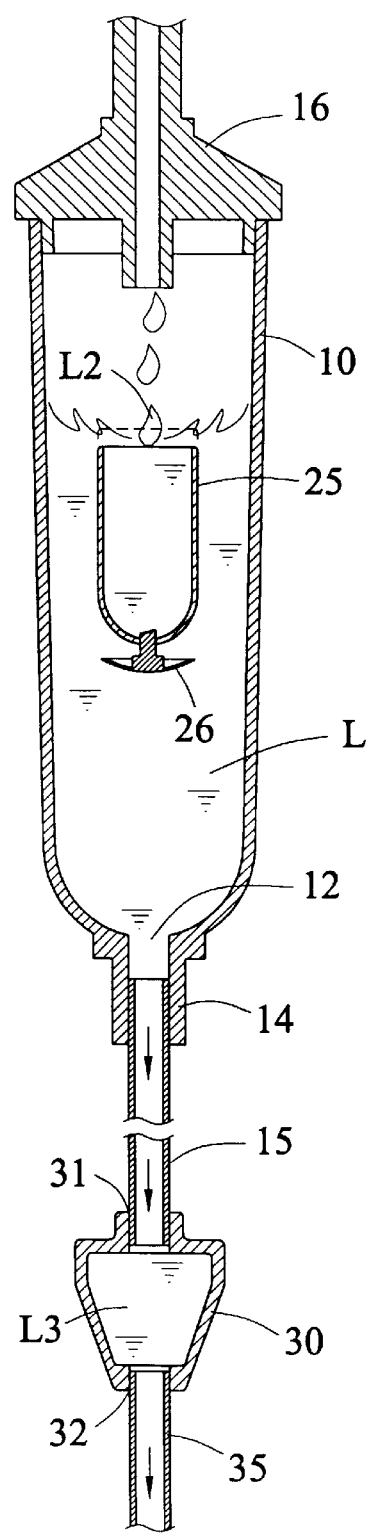
FIG. 8B is similar to FIG. 8A where an abnormal solution dropping occurs.
Figure 8C:
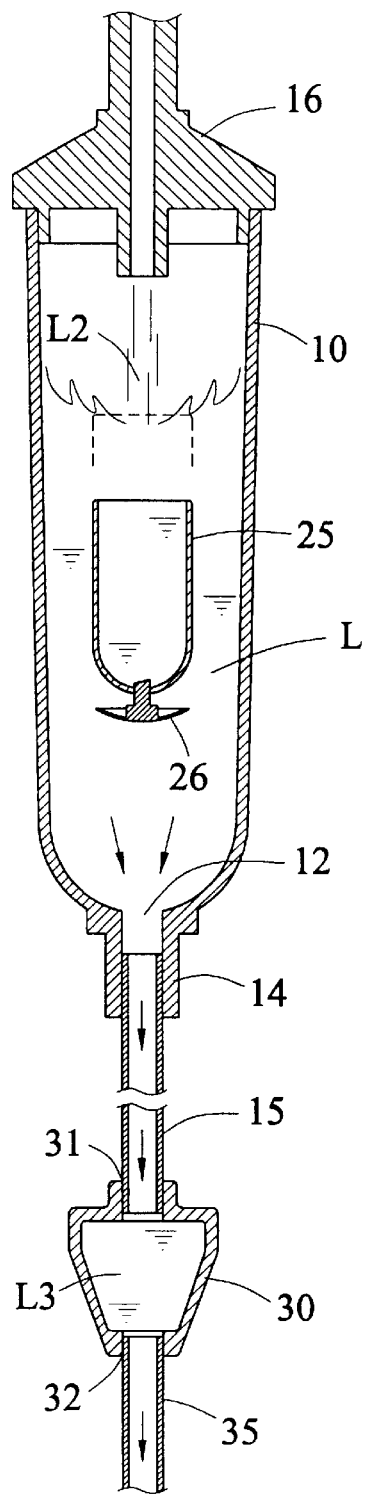
FIG. 8C is similar to FIG. 8A where the float member is going to fall.
Figure 8D:
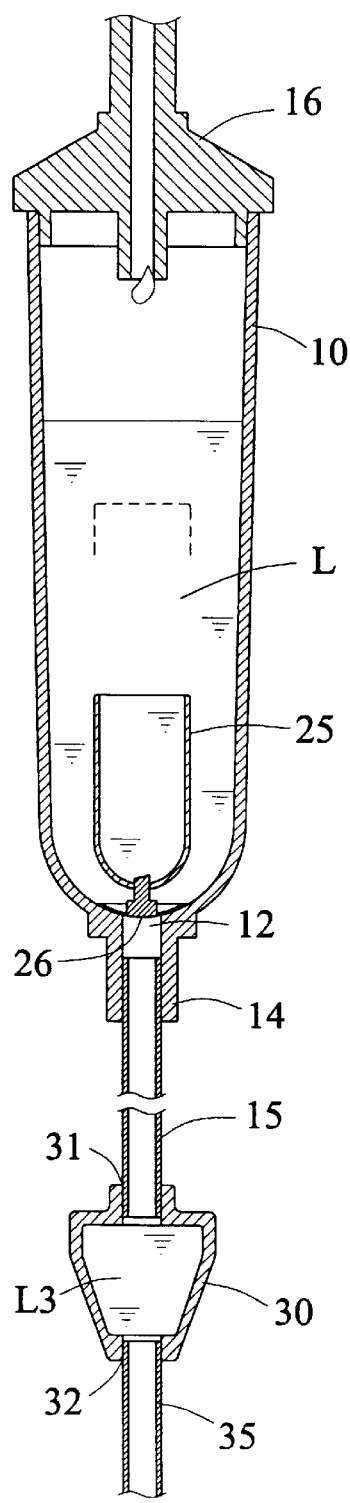
FIG. 8D is similar to FIG. 8A where float member clogs the exit of drip chamber.
Figure 9A:
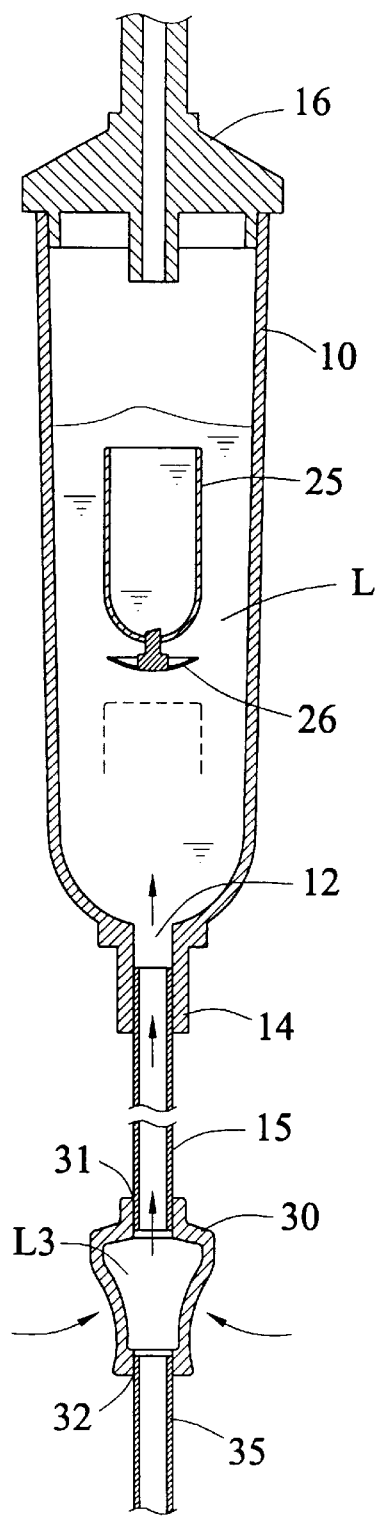
FIG. 9A is a cross-sectional view depicting that the float member is forced to move up by squeezing a reservoir shown in FIG. 8A.
Figure 9B:
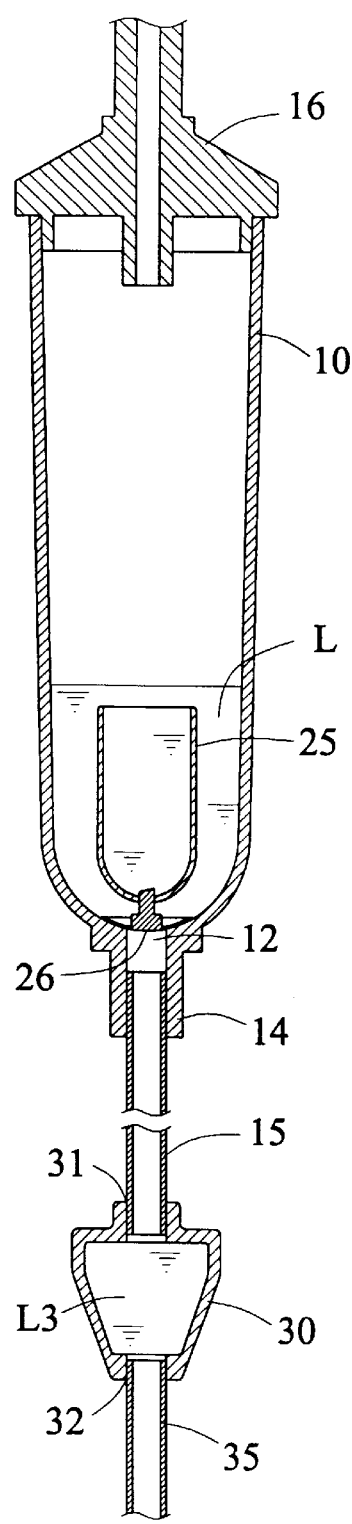
FIG. 9B is similar to FIG. 8A where solution in the drip chamber is nearly used up.
Figure 10:
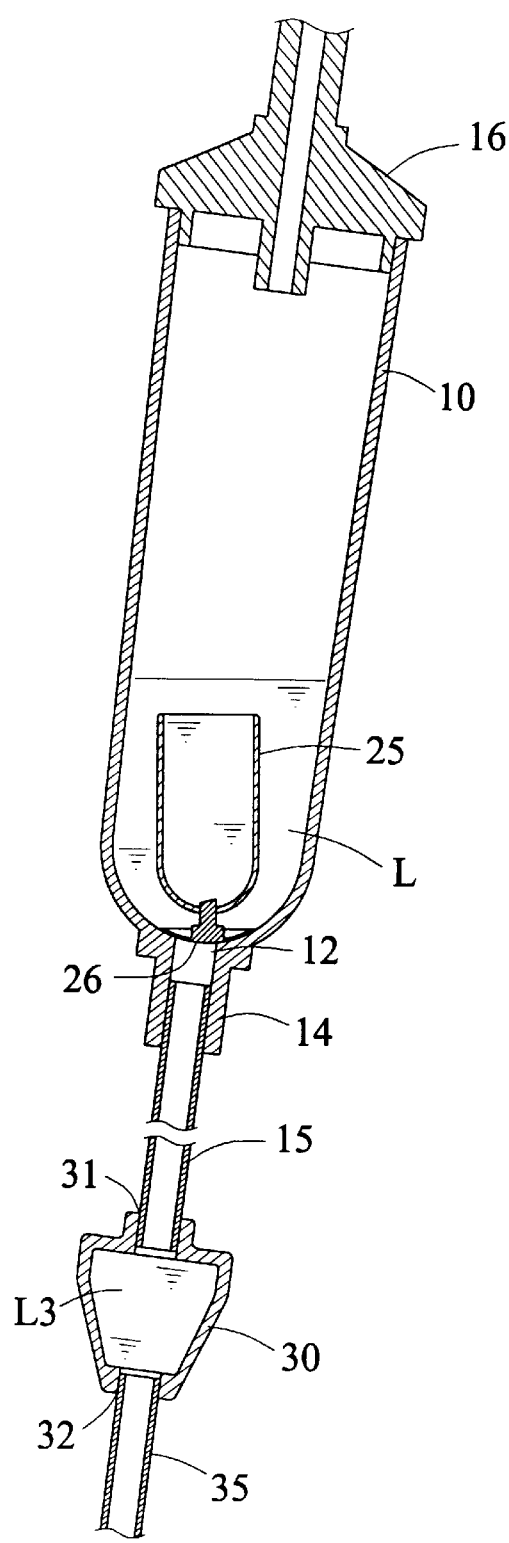
FIG. 10 is similar to FIG. 8A where the bottom of float member still adheres to fluid exit even when float member is slanted.

Referring to FIG. 7, the use of the second embodiment of FIG. 6 will now be described. As shown, IV fluid in a container 60 enters drip chamber 10 through the tip of the drip chamber 10. IV fluid then passes down drip chamber 10, through plastic first tube 15, reservoir 30, second tube 35 and a manual flow controlling device 40, and then goes to a needle 50 in the end of IV flow controlling device. After the float member 20' comprising a shell 25 and a downwards extending convex diaphragm 26 has been set, infusion will then begin.

Referring to FIGS. 8A to 10, It is emphasized that float member 20' comprised of shell 25 and thinner downwards extending convex diaphragm 26 has substantially the same effect as the float member 20 shown in the first embodiment (see FIGS. 2A to 4). Moreover, the provision of thinner downwards extending convex diaphragm 26 makes the clogging of exit of the drip chamber more effective. As to further details of the operation of the second embodiment, it is omitted herein for the sake of brevity.

While the invention herein disclosed has been described by means of specific embodiments, numerous modifications and variations could be made thereto by those skilled in the art without departing from the scope and spirit of the invention set forth in the claims.

What is claimed is:

1. An intravenous (IV) flow controlling device disposed in a drip chamber having an exit in a bottom, the flow controlling device comprising a flexible float member having a specific gravity less than one and an outer diameter smaller than a diameter of the drip chamber, the float member including an open upper portion and a hemi-spherical bottom portion, a wall thickness of the hemi-spherical bottom portion being thinner than a wall thickness of the upper portion of the float member, wherein the float member is submerged as fluid fills the drip chamber, fluid flowing through the exit of the drip chamber causing the float member to fall, thereby stopping fluid flowing through the exit when the flexible bottom portion of the float member blocks the exit of the drip chamber when fluid in the drip chamber is used up.

2. The device of claim 1, further comprising a flexible reservoir having one end coupled to the exit of the drip chamber.

3. The device of claim 2, wherein the reservoir comprises a first tube coupled between the exit of the drip chamber and a top opening of the reservoir and a second tube coupled to a bottom opening of the reservoir such that squeezing the reservoir forces solution stored in the reservoir to flow through the first tube in a reverse direction to disengage the float member from the exit of the drip chamber.

4. The device of claim 1, wherein the float member further comprises an annular flange on a top periphery.

5. The device of claim 1, wherein the float member has a cup configuration.

6. An intravenous (IV) flow controlling device disposed in a drip chamber having an exit in the bottom, the flow controlling device comprising a flexible open container having a specific gravity less than one and an outer diameter smaller than a diameter of the drip chamber, the container including a shell upper portion and a hemi-spherical diaphragm bottom portion, a wall thickness of the hemi-spherical diaphragm bottom portion being thinner than a wall thickness of the shell upper portion of the flexible open container, wherein the flexible open container is submerged as fluid fills the drip chamber, fluid flowing through the exit of the drip chamber causing the flexible open container to fall, thereby stopping fluid flowing through the exit when the bottom portion of the container blocks the exit of the drip chamber when fluid in the drip chamber is used up.

7. The device of claim 6, further comprising a flexible reservoir having one end coupled to the exit of the drip chamber.

8. The device of claim 7, wherein the reservoir comprises a first tube coupled between the exit of the drip chamber and a top opening of the reservoir and a second tube coupled to a bottom opening of the reservoir such that squeezing the reservoir forces solution stored in the reservoir to flow through the first tube in a reverse direction to disengage the container from the exit of the drip chamber.

9. The device of claim 6, wherein the container further comprises an annular flange on a top periphery.

10. The device of claim 6, wherein the shell upper portion further comprises a hole in a bottom thereof and wherein the diaphragm bottom portion has an upper stud inserted into the hole for securing the diaphragm bottom portion to the shell member.

* * * * *